(12) United States Patent
Valencia et al.

(10) Patent No.: US 9,157,848 B2
(45) Date of Patent: Oct. 13, 2015

(54) DING DETECTION SYSTEM

(71) Applicant: FORD GLOBAL TECHNOLOGIES, LLC, Dearborn, MI (US)

(72) Inventors: Carlos Gonzalez Valencia, Cuautitlan Izcalli (MX); Ana Belen Flex Villalba, Cuautitlan Izcalli (MX)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 370 days.

(21) Appl. No.: 13/629,777

(22) Filed: Sep. 28, 2012

(65) Prior Publication Data

US 2014/0090455 A1 Apr. 3, 2014

(51) Int. Cl.
*G01N 19/08* (2006.01)
*G01N 3/28* (2006.01)
*G01B 5/28* (2006.01)

(52) U.S. Cl.
CPC *G01N 19/08* (2013.01); *G01B 5/28* (2013.01); *G01N 3/28* (2013.01)

(58) Field of Classification Search
None
See application file for complete search history.

(56) References Cited

U.S. PATENT DOCUMENTS

| 4,920,385 | A | * | 4/1990 | Clarke et al. | 356/237.2 |
| 5,709,826 | A | * | 1/1998 | Greenberg | 264/40.1 |
| 6,088,093 | A | * | 7/2000 | Greenberg | 356/237.3 |
| 6,219,930 | B1 | * | 4/2001 | Reid | 33/562 |

* cited by examiner

Primary Examiner — Robert R Raevis
(74) Attorney, Agent, or Firm — Joseph E. Root

(57) ABSTRACT

A method and system is provided to detect deformations on a sheet metal panel. The method includes swiping the sheet metal panel's surface through a screening material to screen the deformations present on the sheet metal panel's surface, thereby establishing screened deformations. Further, rubbing an area around the screened deformations through a stone material determines the size of the screened deformations. Finally, measuring the size of screened deformations according to a measuring rule establishes a nature of the screened deformation.

9 Claims, 5 Drawing Sheets

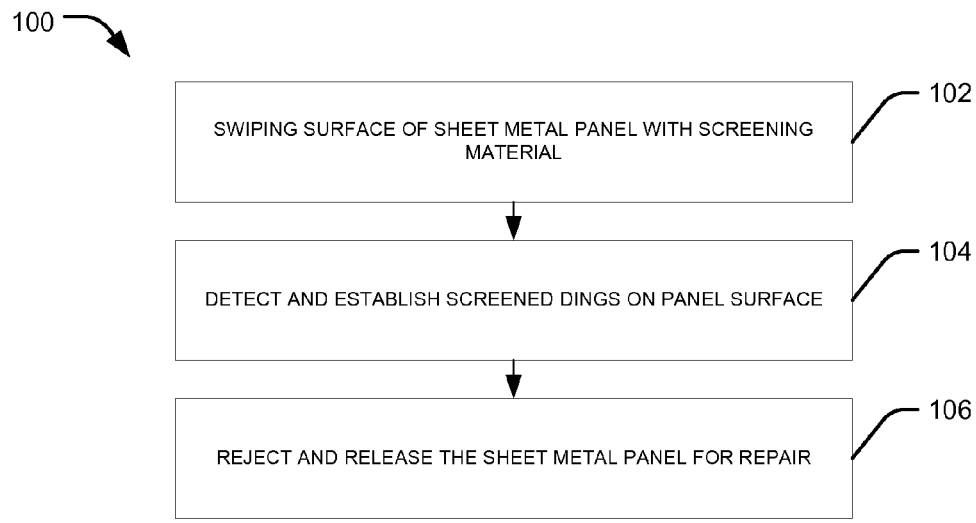
PRIOR ART
FIG. 1
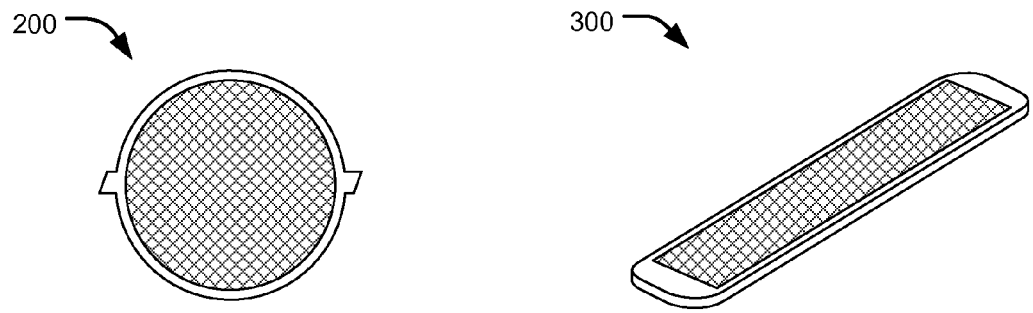
FIG. 2
FIG. 3

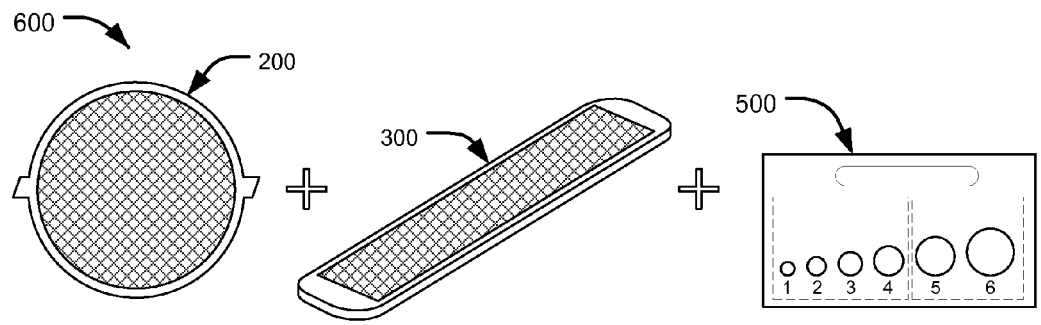
FIG. 6
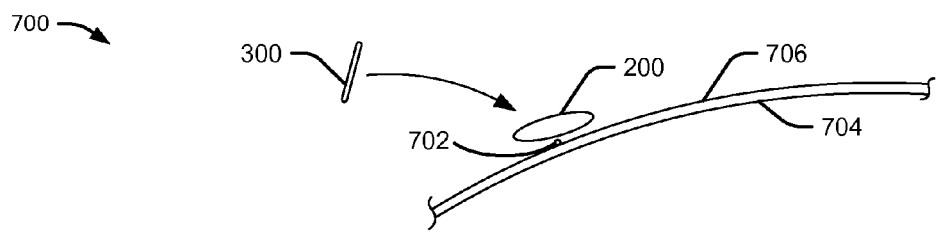
FIG. 7A
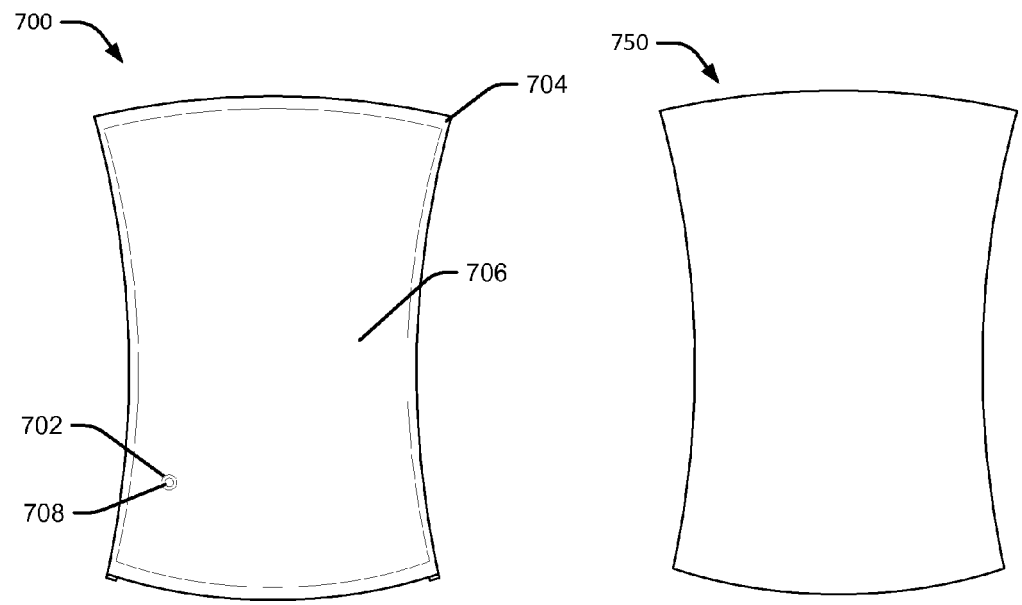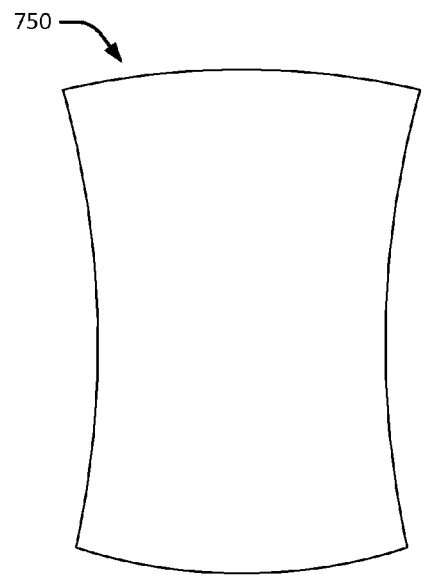
FIG. 7B          FIG. 7C

DING DETECTION SYSTEM

BACKGROUND

This invention relates generally to detection of deformations in the form of dings on sheet metal surfaces, and, more particularly, to detect a nature of the detected ding.

Manufacturing operations involving sheet metals based materials, panels or products, are observed to have undergone considerable advances and improvements over the years. During the manufacturing operations on sheet metals, however, certain undesirable visual deformations are observed on the sheet metal surfaces before the product's completion. Some of these deformations are classified as burrs, wrinkles, slivers, and other visual surface defects, caused possibly because of die and/or tool defects. Out of these, some defects are classified as dings, which are witnessed in a substantial amount by shop floor technicians working on the sheet metal based products. In certain cases, the sheet metal dings found may be as high as 60-65% out of all the defects encountered. Ding formations on sheet metal surfaces, therefore, form a major portion of defects found during a conventional sheet metal manufacturing operation, causing excessive inventory and repair, or even rejection of the sheet metal product, at times.

Conventionally, detection of such dings includes a process of swiping the sheet metal surface with a screening material. In general, all sheet metal surfaces, when detected with dings, are either rejected or carried away for repairs without considering their affect on the final product. A relatively large percentage of dings detected through the above noted method, in contrast, include a considerable variation in their physical sizes and dimensions. Accordingly, dings detected having considerably small dimensions may not affect a final work output, after a paint job, and thus may not be sent for repairs. Moreover, experiments have substantiated that a ding detected through the above process, but having a dimension less than a particular predetermined calculated value or standard, need not be seen as one that requires a repair. This, in general, is observed to be true once the related sheet metal product is formed into a final product and paint is applied to it.

There thus remains room for improvements in reducing the number of sheet metal rejections, thereby minimizing needless inventory and stock, repairs on which may not particularly affect the final work output.

SUMMARY

One embodiment of the present disclosure describes a method to detect deformations on a sheet metal panel. The method includes swiping the sheet metal panel's surface with a screening material to screen the deformations present on the sheet metal panel, thereby establishing screened deformations. Thereafter, the method includes rubbing an area around the screened deformations with a stone material to determine the size of the screened deformations, and finally, measuring the screened deformations according to a measuring rule establishes a nature of the screened deformation.

Another embodiment of the present disclosure describes a ding detection method on a sheet metal panel. The method includes swiping the sheet metal panel with a screening material to screen dings present on the sheet metal panel, establishing screened dings, and thereafter, rubbing an area around the screened dings with a stone material to determine the size of the screened dings. The rubbing produces an outline around the dings, forming a halo around the screened ding. Lastly, the method provides for measuring the screened dings according through a measuring rule, establishing a nature of the screened dings. More particularly, the measuring rule includes a series of markers to gauge the screened dings, where gauging the size of the formed halo enables measurement of the screened dings. The measuring rule, accordingly, forms an ordinal measuring system.

Certain embodiments of the present disclosure describe a ding measurement system for a sheet metal panel. The system includes a screening material, which is adapted to be swiped over the sheet metal panel's surface to screen dings, thereby establishing screened dings. Further, a stone material is provided which is configured to be rubbed around an area of the screened dings to determine the size of the screened dings. More specifically, rubbing the stone material around the screened dings produces an outline around the dings, which forms a halo. A measuring rule is configured to measure the screened dings through the obtained halo, establishing a nature of the screened dings. Moreover, the measuring rule, forming an ordinal measuring system, is configured to include a series of markers to gauge the screened dings.

BRIEF DESCRIPTION OF THE DRAWINGS

The figures described below set out and illustrate a number of exemplary embodiments of the disclosure. Throughout the drawings, like reference numerals refer to identical or functionally similar elements. The drawings are illustrative in nature and are not drawn to scale.

FIG. 1 is a flowchart depicting a conventional ding detection method carried out on a sheet metal.

FIG. 2 is an exemplary screening material according to the aspects of the present disclosure.

FIG. 3 is an exemplary stone material according to the aspects of the present disclosure.

FIG. 6 is an exemplary ding detection system according to the aspects of the present disclosure.

FIG. 7A is a side view of an exemplary application of the ding detection method carried out on the exterior a vehicular roof structure.

FIG. 7B is top view of an exemplary application of the ding detection method carried out on the exterior of a vehicular roof structure.

FIG. 7C is an exemplary template according to the aspects of the present disclosure.

OVERVIEW

Figure 4:
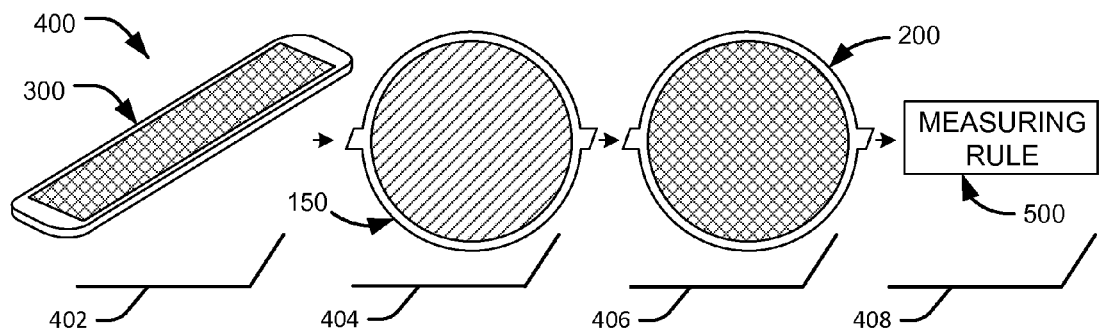
FIG. 4 is an exemplary surface evaluation evolution process.

In general, the present disclosure describes methods and systems to detect dings on a sheet metal surface, such that a ding detected may enable the determination of the requirement of a repair or release of the related sheet metal materials, such as a sheet metal panel. To this end, a screening material is swiped over the sheet metal surface to establish dings and thereafter, a stone material is rubbed over the screened dings. Measurement of the physical dimensions of the screened dings is subsequently carried out, allowing the determination of release or repair of the sheet metal panel, according to a predetermined standard.

Exemplary Embodiments

Aesthetic value and surface quality of sheet metal based products and panels are, in general, a factor that builds up market value and reputation of a related product. Therefore, even a considerably small deformation or defect, occurring through forming processes, etc., may become a factor for the sheet metal panel's rejection before the end of the line (EOL), or before a painting operation is carried out, during manufacturing. As noted above, a substantial portion of these defects or deformations is generally classified as sheet metal dings, which generally appear as a black spot. Commonly, upon the detection of an apparent surface defect or a ding, sheet metal panels, even when partly formed, are sent over for repairs and/or rework. On certain occasions, such sheet metal panels are completely rejected. Such repairs, reworks, and rejections, increase the amount of inventory, causing shortages in storage spaces, excessive consumption, and waste of resources, time, etc. Furthermore, production targets are affected because of repeated repairs and reworks.

Obtaining a minimum or an optimum amount of inventory is desirable in sheet metal based industries that manufacture sheet metal based materials. This requires considerable efforts from shop floor technicians, personnel, and other stakeholders, to achieve minimum ppm (parts per million) rejections and/or repairs.

To describe a conventionally practiced ding detection method in detail, FIG. 1 presents a flowchart 100. According to FIG. 1, during a first detection stage 102, an operator swipes a screening material (described later) over a surface of a sheet metal panel. This stage is carried out as part of a swiping process. The screening material conventionally applied includes a property to detect dings during the swiping process, and therefore, screens the sheet metal surface for dings. Screened dings are thereby established at a subsequent stage 104. Finally, at stage 106, after the establishment of screened dings, the sheet metal panel is sent for repairs and/or rework to remove the dings, so that the partly manufactured panel may be released to the next production stage.

FIG. 2 depicts a conventionally known and applied screening material 200, such as the widely applied 3M screen 320, which is configured to be swiped over the sheet metal surface to detect dings. In detail, the screening material 200 is a flexible cloth type of material, which is generally shaped in the form of a disc that is abrasive in texture, but smooth enough to avoid scratches on a sheet metal surface, when employed for swiping. The screening material 200 can be applied on both wet and dry surfaces, and in both cases, the swiping operation is observed to effectively screen dings present on the sheet metal surface. More particularly, the screening material 200 may be a resin bonded to a strong flexible cloth, which may be applied for sanding applications as well. In physical dimensions, the screening material 200 is small enough to fit into the hands of an operator who is appointed to swipe the screening material 200 over the sheet metal surface. Moreover, the configurations of the screening material 200 may enable the application of automated processes to carry out the swiping process as well. As noted above, the screening material 200 is configured in such a way when wiped over the sheet metal surface; the screening material 200 will enable the visualization of defects and deformations, like dings, to the naked eye. The screening material 200, being well known to the skilled in the art, will not be discussed further.

A stone material 300, as illustrated in FIG. 3, is configured to be rubbed over the sheet metal surface after the detection of the dings. More particularly, the stone material 300 can be rubbed over the screened dings to ascertain a physical dimension of the detected dings. In structure, the stone material 300 is a hard material that, when rubbed over the screened dings, shows every defect on the sheet metal surface. In the present disclosure, an 'India Sheet Metal Stone' is applied for the rubbing process. More specifically, a rubbing of the stone material 300 is configured to produce an outline around the screened dings, where the outline forms a halo 708 (shown in FIG. 7B), which thereby permits a measurement and determination of the size or the physical dimensions of the screened ding. Moreover, the stone material 300 being well in the art will not be discussed further.

Turning to FIG. 4, a surface evaluation evolution process 400 will now be described. Over the years, the surface evaluation evolution process 400 for sheet metal has undergone continuous improvements (CI). Initially, as part of a learning process, all sheet metal panels were released to the next production stage only when all the detected dings on the sheet metal surface, irrespective of the ding size, were repaired. Here, the defects or dings were detected by applying only the stone material 300. Such detection included the rubbing of the stone material 300 all over the sheet metal surface. This consumed excessive time and effort. A period 402 depicts a corresponding usage range. To lessen the time consumed to detect the dings, a screening material 150 was introduced, at a later stage, into the ding detection procedures. The screening material 150, which may be a well-known 3M screen 1000, improved upon the time for its application over the sheet metal surface, and resulted in a faster detection of dings, irrespective of the ding size, requiring considerably lesser effort as well. This usage range, being depicted through a period 404, quickened the application time, however, the detection of even negligibly sized dings, increased the amount of sheet metal panel repair and rework. Subsequently, a period 406 was incorporated, through which a further improvement was made to the ding detection process. The screening material 200, described earlier in this disclosure, was introduced in place of the screening material 150. This detected dings having substantially larger physical dimensions, than the ones detected by the screening material 150. This thus reduced the number of sheet metal panels being sent for repairs. The aim of this improvement was to ignore the small sized dings that do not affect the aesthetics of the final product. Substantial improvement were however still not observed, as this method also resulted in every observed or screened defect to be repaired, still leading to considerably excessive repairs and reworks. Moreover, with the above systems in place, it was not known which of the screened dings would appear as a surface defect after paint is applied on the sheet metal panel, and, accordingly, which of the dings caused an unnecessary repair. With the above requirements, the period 408 defines the scope of the present disclosure, proposing the idea of combining the screening material 200, the stone material 300, and a measuring rule 500 (described in FIG. 6), to gauge the detected dings' size, and accordingly, the nature of the screened or detected ding. Here, the nature of the ding is understood to mean whether the ding needs a repair/rework, or not. Accordingly, the system and the method disclosed in period 408 advantageously minimizes inventory and wastages of the sheet metal products and panels, to a significant extent, by reducing excessive repairs and reworks originating from screened defects and deformations that do not actually require repairs.

More particularly, the ding detection system according to the present disclosure includes the application of a predetermined standard through which the dings are gauged, and their nature is established, which, in particular, prescribes and categorizes the dings based on whether there is a requirement for a rework/repair over a sheet metal panel, or not. Such a system, if effectively installed in place, minimizes criteria confusion and other overheads associated therewith, encountered during manufacturing processes.

Figure 5A:
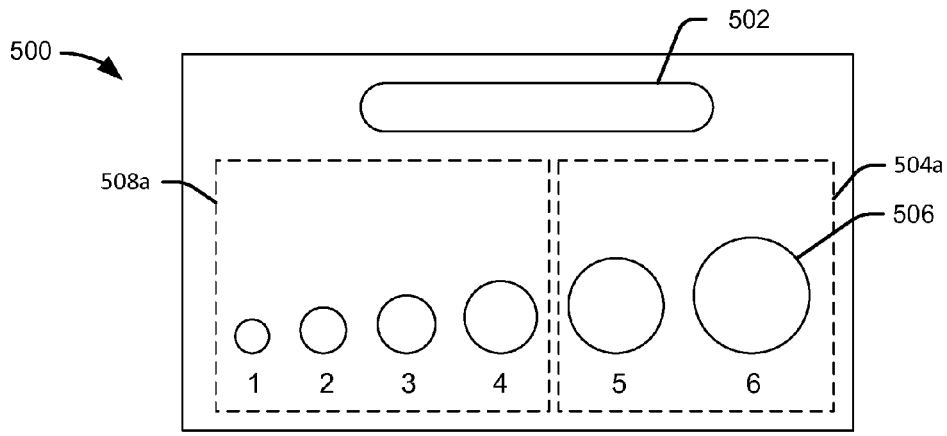
FIG. 5A is an exemplary measuring rule according to the aspects of the present disclosure.

Accordingly, referring to FIG. 5A, the predetermined standard, referred to as the measuring rule 500, is described. In detail, the measuring rule 500 is a scale or a reference ruler, against which ding measurements are matched, calibrated, and determined. The measuring rule 500, therefore, forms an ordinal measuring system. In the depicted embodiment, the measuring rule 500 is transparent flexible material, and thus can be plastic, enabling ease in storage, retrieval, and use. The measuring rule 500 includes a title slot 502 to differentiate different measuring rules, and includes a series of markers 506, which form the entire line-up of an in-built marking reference, such as the ones found in conventional measuring scales.

In the depicted embodiment, the measuring rule 500 includes 6 markers, starting from a $1^{st}$ marker, which measures against the smallest ding, all the way to the largest marker, which is the $6^{th}$ marker, which measures against the largest ding. This configuration may optionally be different for different markers applied in varied sheet metal panels, components, etc., and may vary from practice-to-practice, as well. Regions 504a and 508a are denoted and disposed for the determination of the nature of the ding detected, establishing the requirement of the sheet metal panel to be sent for repairs, or not.

As an example, if a ding is detected to fall under the $5^{th}$ marker, which is included in the region 504a, it can be understood that the ding detected on the sheet metal panel is considerably large, and thus needs to be sent for repairs and reworks. In contrast, if the ding is detected to fall under the $3^{rd}$ marker, which is included in the region 508a, repairs on the ding may be avoided. All dings falling within the region 508a may be understood to have a considerably small size that may not affect a final work product after a paint job is performed over the related sheet metal panel. On the other hand, dings falling under the region 504a are understood to have dimensions big enough to affect the aesthetic appeal of the product output.

Figure 5B:
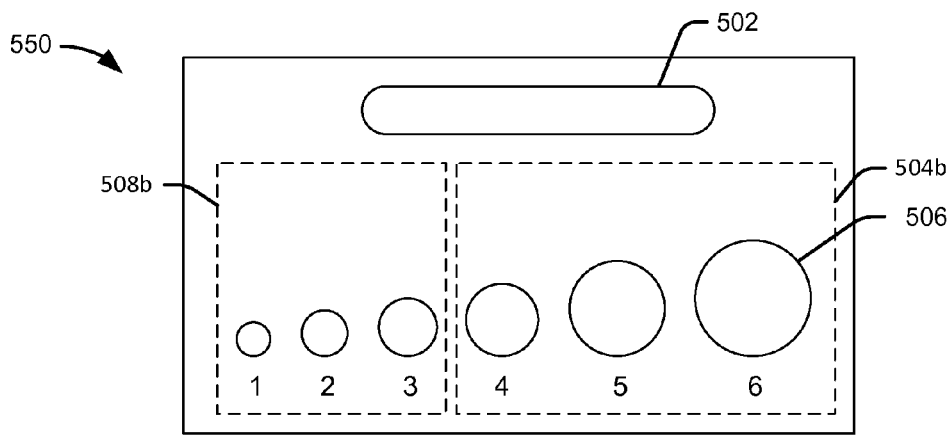
FIG. 5B is an embodiment of the aspect depicted in FIG. 5A.

Likewise, in FIG. 5B, a measuring rule 550 includes structural configurations similar to the one depicted in FIG. 5A, but includes an embodiment of a change in the regions 504a and 508a depicted in FIG. 5A. Accordingly, the measuring rule 550 depicted in FIG. 5B depicts a re-calibrated measuring rule 550, having different regions 504b and 508b, to gauge the nature of the detected ding. Such re-calibrations are discussed below.

In another embodiment, color-coding can be introduced to visually differentiate the markers 506 from each other. In addition, the number of markers may be varied, as well. It is thus well understood that the embodiment of the measuring rule 500 depicted in FIGS. 5A and 5B is not meant to be limiting in any way, and accordingly the size, material, pattern, marking, etc., may differ according to a desired practice. Moreover, the regions 504a and 508a can be marked over the measuring rule 500 with an erasable ink or a permanent ink. It is understood that the application of an erasable ink enables frequent changes in the regions, while repeatedly calibrating the measuring rule 500 according to different requirements.

Turning to FIG. 6, an exemplary ding detection system 600, according aspects of the present disclosure, is depicted. As noted above, the system 600 includes the components such as the screening material 200, the stone material 300, and the measuring rule 500, together forming the elements described for the period 408 (depicted in FIG. 4), and thereby forming a mechanism to effectively screen dings. As would now be known, the system 600 works to minimize inventory by enabling the determination of only those sheet metal panels that require a repair, while the ones with considerably small defects may be ignored, as they would go unnoticed to the human eye, after a paint job is performed. It is understood that the structure and other details of the components of system 600 would remain similar to the ones already discussed in the application, and thus their structure and other embodiments will not be discussed further. Appropriate calibrations are however required to be carried out to the measuring rule 500, to accurately identify the panels that actually require a repair, and the ones that do not.

Referring to FIG. 7A, FIGS. 7B, and 7C, a working 700 of the ding detection system 600 is described. More specifically, the figure illustrates a sheet metal panel 704, having a sheet metal surface 706, which in turn includes a ding 702. In operation, an operator first swipes the screening material 200 over the sheet metal surface 706, as shown, and thereafter, brings over the stone material 300 and rubs it over the sheet metal surface 706. More particularly, the rubbing is performed over the ding 702, to obtain an outline around the ding 702. The outline forms a halo 708, as shown in FIG. 7B, which depicts a relative size of the ding 702. Subsequently, the measuring rule 500 is brought over the formed halo 708, to measure the halo's size, thereby gauging the size of the screened defect. The halo 708, depicting a relative size of the ding 702, enables technicians, shop floor operators, and other stakeholders, to decide whether the sheet metal panel 704 requires a repair, or not, or in effect, which of the screened dings actually require a repair.

Figure 8:
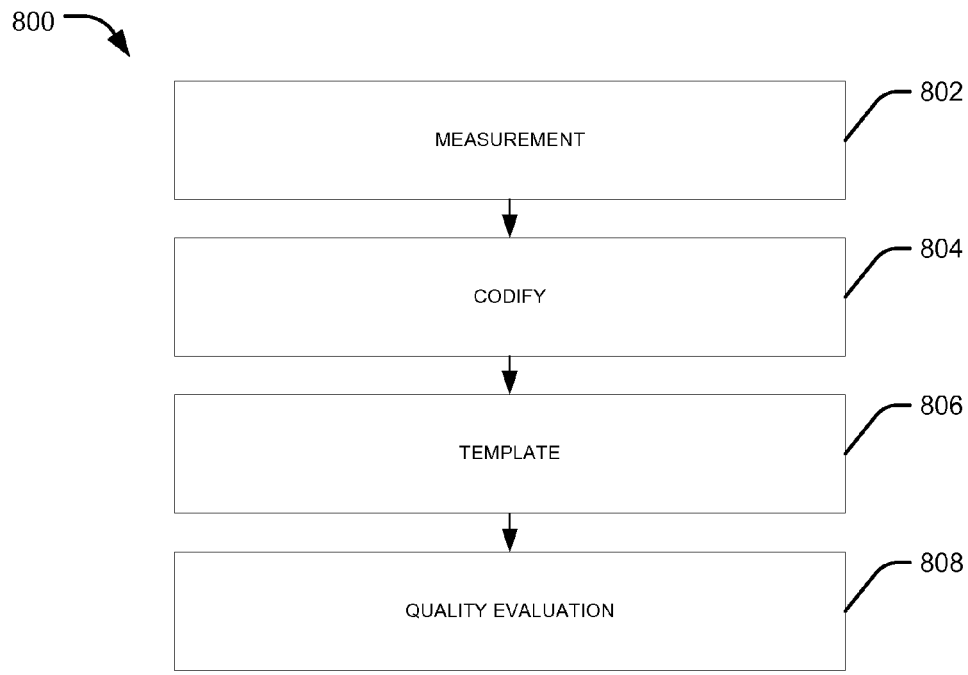
FIG. 8 is a flowchart depicting an exemplary trial and calibration process of the measuring rule.

The decision to allow a material, such as the sheet metal panel 704, to be sent for repairs when gauged through the measuring rule 500, requires the regions 504a and 508a in the measuring rule 500 to be calibrated as well. Such a calibration is enabled through a series of trials, which enables the measuring rule 500, in particular, to be appropriately calibrated. According to the aspects of the present disclosure, over 700 trials were conducted to obtain an appropriate measuring rule 500, and more specifically, to determine out of which of the regions 504a and 508a, were the markers 506 required to be categorized into. FIG. 8 depicts an exemplary trial process 800 that was carried out to calibrate the measuring rule 500.

At the trial process' first stage 802, operators involved measure the ding 702, or multiple such dings, detected through the ding detection system 600, and more particularly, through the measuring rule 500, to obtain a ding level. Thereafter, the operators codify the measured ding 702, or a plurality of such dings, at a subsequent stage 804. The codification process involves marking the ding's physical dimensions around the screened dings, on the sheet metal panel 704, through a measured score obtained through the measuring rule 500. The measured score can exemplarily be in the form of A5, A6, B1, etc., where, "A" and "B" stand for the zone on the sheet metal panel 704, while 5, 6, and 1, represent the scores obtained through the markers 506. Next, at stage 806, the operators involved, record the codifications on a template 750, depicted in FIG. 7C, to mark the measurement and position of the ding 702. Here, the template 750 may be a transparent flexible material, preferably made of plastic, the dimensions and structure of which is equivalent to the sheet metal panel's dimensions and structure. In application, after the codification process, the template 750 is made to cover the sheet metal panel, enabling the operators to establish marks on the template 750, corresponding to the markings obtained through the codification process on the sheet metal panel 704. Once this is performed, the template 750 is removed and the sheet metal panel 704 is made to undergo regular operations, as part of the production process. Thereafter, as processes such as surface treatment and painting operations are carried out on the sheet metal panel 704, the codification marks would disappear, and eventually the final product is obtained as output. The operator, at this stage, covers the sheet metal panel 704 with the template 750 again, and performs checks and compares the portion where codification marks were disposed initially. Such a checking is performed as part of a quality evaluation stage 808 through the markings made on the template 750, to check whether the ding originally disposed actually appears after the paint job, or affects the final product in any way. It is understood that the operators and the checking personnel involved here include body engineers, stamping quality engineers, respective team leaders, surface inspectors, auditing personnel, shop floor technicians, etc., and primarily, the entire quality team. An analysis of the dings that appear and the ones that do not appear enables technicians and engineers to calibrate the measuring rule 500.

Figure 9:
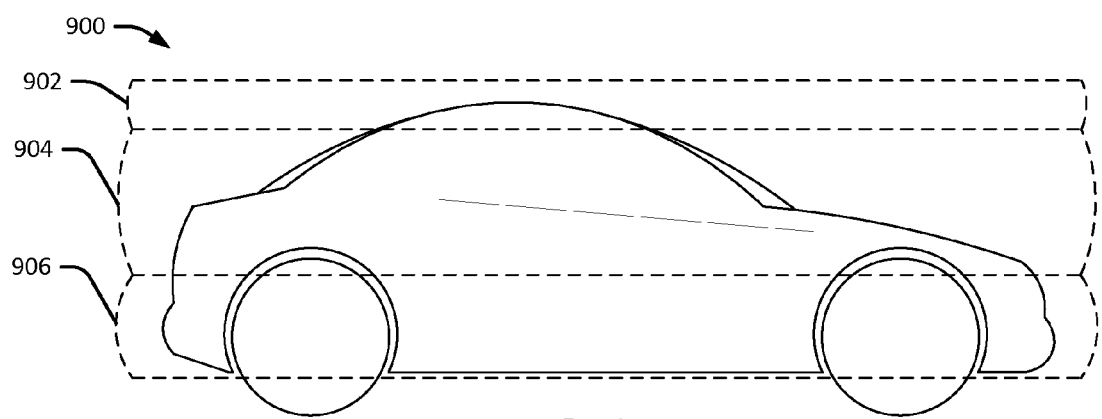
FIG. 9 is an exemplary application of the ding detection method performed on a vehicular body according to the aspects of the present disclosure.

Turning now to FIG. 9, an exemplary application of the ding detection system 600 is described, which can be performed on a vehicular body 900, which is in turn substantially made from sheet metal. To keep a ding detection system optimized, the vehicular body 900 is configured to include 3 distinct regions, namely, a low visibility region 902, a high visibility region 904, and a medium visibility region 906. More particularly, the optimization includes the related ding detection system to be applied differently in the 3 different regions. Accordingly, the region 902, which includes the vehicle roof, may apply the ding detection system 600, as described above, while the region 904 and 906 may include ding detection systems that were conventionally applied. This is because the region 902, low visibility region, stays substantially out of a line of sight from human viewing in general conditions, and accordingly, the presence of dings that were considerably small, and which were not repaired, would remain substantially invisible. The regions 904 and 906, however, falling under the considerably visible regions, may continue to follow the conventional ding detection methods, which prescribed all detected dings to be repaired. The method described herein reduces inventory of the vehicle roof, and other portions lying with the region 902, to a fairly large extent, as observed through repeated trials and experiments, which in turn provide reduced wastages and resource utilization.

Figure 10:
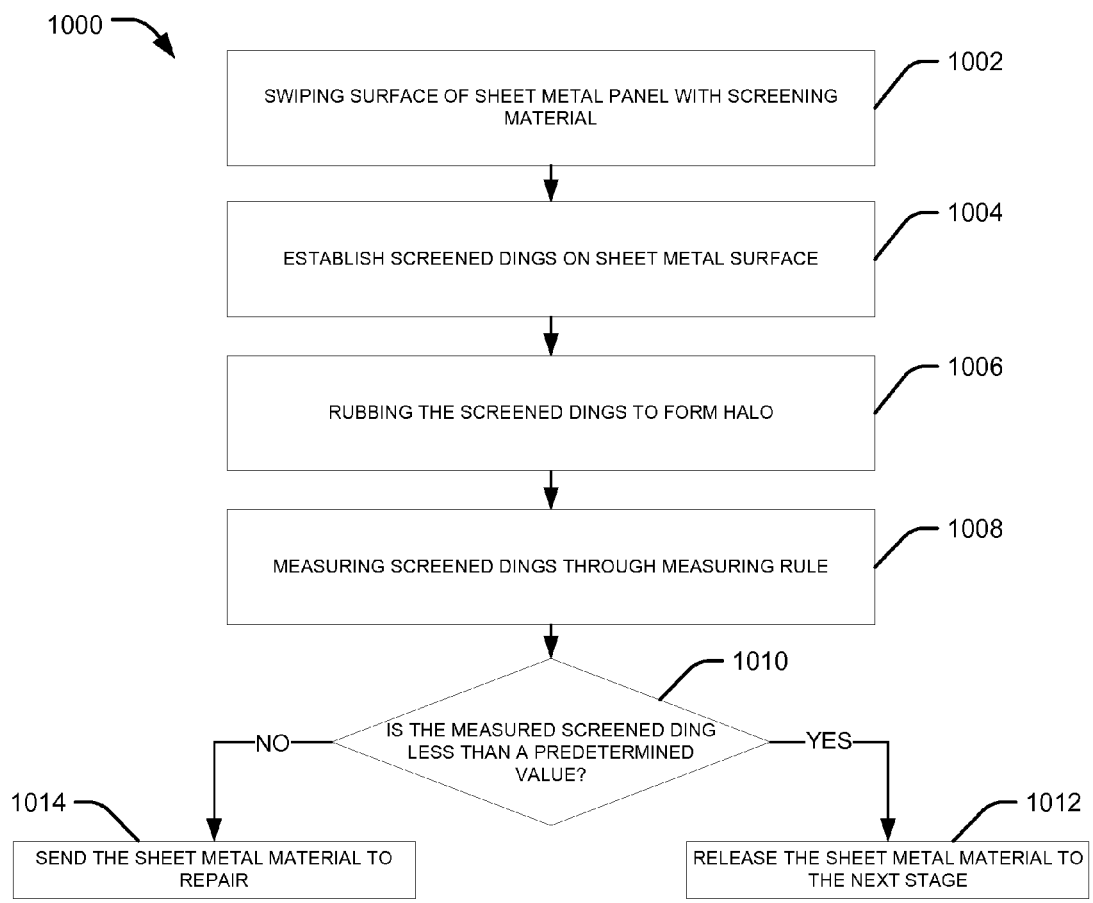
FIG. 10 is an exemplary flowchart depicting the ding detection method according to the aspects of the present disclosure.

The system 600 set out above is described through a method 1000, as well in the following description of FIG. 10, which includes a flowchart. It is understood that the description discussed for the method 1000 will be similar to the description discussed for FIGS. 7A and 7B.

Accordingly, at a first stage 1002 of the method 1000, an operator swipes the surface 706 of the sheet metal panel 704 with the screening material 200. The swiping of the sheet metal surface 706 with the screening material 200 enables the establishment of detected or screened dings at stage 1004. As noted above, generally, dings over a sheet metal surface, such as the sheet metal surface 706 appear as a black spot. Subsequently, at the next stage 1006, the operator rubs the stone material 300 over the detected or screened dings, which enables the production of an outline around the screened dings, the outline thereby forming a halo 708 (depicted in FIG. 7). Thereafter, the operator measures and gauges a size of the halo 708 obtained through the measuring rule 500, and obtains a level of the screened dings according to the markers 506 provided on the measuring rule 500. This occurs at stage 1008. Once the ding level is achieved, in the following stage 1010, the operator gauges whether the ding level obtained is lesser than a predetermined standard (obtained according to the regions 504*a* and 508*a* in the measuring rule 500), which in turn determines whether the dings found would cause the sheet metal panel 704 to be sent to repairs or not. Accordingly, if the ding level is greater than the predetermined standard then the sheet metal panel 704 is sent for repairs at stage 1014, while on the contrary, when the ding level is found to be lesser than the predetermined standard, the sheet metal panel 704 is released to the next production cycle, at stage 1012.

The specification has set out a number of specific exemplary embodiments, but those skilled in the art will understand that variations in these embodiments will naturally occur in the course of embodying the subject matter of the disclosure in specific implementations and environments. It will further be understood that such variation and others as well, fall within the scope of the disclosure. Neither those possible variations nor the specific examples set above are set out to limit the scope of the disclosure. Rather, the scope of claimed invention is defined solely by the claims set out below.

We claim:

1. A method to identify and classify deformations on a sheet metal panel, the method comprising:
    applying an abrasive screening material to the sheet metal panel's surface to identify deformations present on the sheet metal panel, the screening material being in the form of an object having dimensions substantially smaller than the dimensions of the sheet metal panel, wherein the application of the screening material includes swiping the screening material over the entire surface of the sheet metal panel, the screening material being abrasive in texture but sufficiently smooth to avoid scratching the sheet metal panel, thereby establishing screened deformations;
    rubbing an area around each identified deformations with a tool to determine the size of the identified deformations; and
    measuring the screened deformations employing a measuring rule to classify each identified deformation.

2. The method of claim 1 wherein the step of rubbing further comprises obtaining an outline around the screened deformations through rubbing, the outline establishing a halo.

3. The method of claim 2, wherein the step of measuring further comprises, gauging a size of the halo to measure the screened deformations.

4. The method of claim 3, wherein the measuring rule forms an ordinal measuring system including a series of markers to gauge the size of the halo.

5. The method of claim 1, wherein the deformations are dings.

6. The method of claim 1, wherein classifying each identified deformation includes a categorization of the deformations based on the ones that require a repair and the ones that do not require a repair, wherein the categorization includes measuring the screened deformations according to a predetermined standard.

7. The method of claim 1 further comprising using a template on the sheet metal panel to mark a measurement and position of the deformations.

8. The method of claim 7, wherein the template is a flexible transparent plastic.

9. The method of claim 7, wherein the marks on the template is compared to the sheet metal panel, when the sheet metal panel is formed into an output after a painting operation, enabling calibration of the measuring rule.

\* \* \* \* \*